US008447624B2

(12) United States Patent
Pederson et al.

(10) Patent No.: US 8,447,624 B2
(45) Date of Patent: May 21, 2013

(54) METHODS FOR MANAGING INFECTION RISK INCIDENT TO SURGICAL PROCEDURES IN HEALTH CARE PROVIDER ENVIRONMENTS

(75) Inventors: Cheryl A. Pederson, Eden Praire, MN (US); Jennifer S. Ma, St. Paul, MN (US); Nancy J. Dyslin, Stillwater, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 1873 days.

(21) Appl. No.: 09/729,034

(22) Filed: Dec. 4, 2000

(65) Prior Publication Data
US 2002/0103671 A1 Aug. 1, 2002

(51) Int. Cl.
*G06Q 50/00* (2012.01)
(52) U.S. Cl.
USPC .................................................. 705/2
(58) Field of Classification Search .... 705/2–4; 600/300
See application file for complete search history.

(56) References Cited

U.S. PATENT DOCUMENTS

| | | | | |
|---|---|---|---|---|
| 5,562,448 | A * | 10/1996 | Mushabac | 433/215 |
| 5,937,364 | A * | 8/1999 | Westgard et al. | 702/83 |
| 6,157,853 | A * | 12/2000 | Blume et al. | 600/426 |
| 6,509,730 | B1 * | 1/2003 | Afsah | 324/158.1 |
| 6,662,081 | B1 * | 12/2003 | Jacober et al. | 700/242 |
| 6,827,670 | B1 * | 12/2004 | Stark et al. | 482/9 |
| 2002/0077865 | A1 * | 6/2002 | Sullivan | 705/3 |

FOREIGN PATENT DOCUMENTS

| | | |
|---|---|---|
| JP | 11-85876 A | 3/1999 |
| WO | 00/67189 | 11/2000 |

OTHER PUBLICATIONS

Mangram et al., "Guideline for the Prevention of Surgical Site infection", American Journal of Infection Control, 1999, vol. 27, pp. 97-134.*
Ormond-Walshe, Sarah, "Computerised databases in infection control", Nursing Standard, Jan. 2000, vol. 14, No. 18, pp. 43.*
Skledar et al., "Using a CQI process to change surgical antimicrobial prophylaxis practices", Formulary, Jan. 2000, vol. 35, No. 1, pp. 53.*
Guebbels et al., "An operating surveillance system of surgical site infections in the Netherlands: Results of the PREZIS National Surveillance Network", Infection Control & Hospital Epidemiology, May 2000, vol. 21, No. 5, pp. 311.*
American Association of Nurse Anesthetists (AANA), *Infection Control Guide*, Park Ridge, IL: AANA; revised 1997.
American College of Surgeons, Care of the Surgical Patient, vol. 2: Elective Care, New York, NY: Scientific American; 1988-1993.
American Institute of Architects, Academy of Architecture for health, with assistance from the U.S. Department of Health and Human Services, *Guidelines for Design and Construction of Hospital and Health Care Facilities*, Washington, D.C.: AIA Press; 1996.

(Continued)

*Primary Examiner* — Gerald J. O'Connor
*Assistant Examiner* — John Pauls
(74) *Attorney, Agent, or Firm* — X. Christina Huang

(57) ABSTRACT

The invention provides methods and systems designed generally to managing the risk or occurrence of surgical site infection incident to a surgical procedure. The methods and systems employ perioperative process mapping tools that align, monitor and/or manage the operation of a plurality of health care delivery practices and thereby provide a desired level of infection risk management.

34 Claims, 7 Drawing Sheets

OTHER PUBLICATIONS

American Society of Anesthesiologists (ASA), Committee on Occupational Health of Operating Room Personnel and Task Force on Infection Control, Recommendation for Infection Control for the Practice of Anesthesiology, 2nd ed., Available at www.asahq.org/proinfo/infection.

Association for Professionals in Infection Control and Epidemiology (APIC), Larson EL. APIC guideline for handwashing and hand antisepsis in health are settings, *Am J Infect Control*. 1995; 23:251-269.

Larson EL. Guideline for use of topical antimicrobial agents. *Am J Infect Control*. 1988; 16:253-266.

Lee TB, Baker OG, Lee JT, Scheckler WE, Steele L, Laxton CE. Recommended practices for surveillance. *Am J Infect Control*. 1998; 26:277-288.

Martin MA, Reichelderfer M. APIC guideline for infection prevention and control in flexible endoscopy. *Am J Infect Control*. 1994; 22:19-38.

Rutala WA. APIC guideline for selection and use of disinfectants. *Am J Infect Control*. 1996; 24:313-342.

Sherertz RJ, Streed SA, Gledhill KS. Surgical site infections. In AIPC *Infection Control and Applied Epidemiology*. St. Louis, MO: Mosby; 1996:11-1 to 11-5.

Association for the Advancement of Medical Instrumentation (AAMI), AAMI *Standards and Recommended Practices, vol. 1.1: Sterilization*. Arlington, VA:AAMI; 1998.

Association of periOperative Registered Nurses (AORN), *Recommended Practices & Guidelines*. Denver, CO: AORN; 1999.

Centers for Disease Control and Prevention, Hospital Infection Control Practices Advisory Committee (CDC), Mangram AJ, Horan TC, Pearson ML, et al. Guideline for prevention of surgical site infection, 1999. *Am J Infect Control*. 1999; 27:97-134.

Society for healthcare Epidemiology of America (SHEA), Consensus paper on the surveillance of surgical wound infections: The Society for Hospital Epidemiology of America. The Association of Practitioners in Infection Control, The Centers for Disease Control, The Surgical Infection Society. *Infect ControlHosp Epidemiol*. 1992; 13:599-605.

Surgical Infection Society (SIS), Page CP, Bohen JM, Fletcher JR, et al. Antimicrobial prophylaxis for surgical wounds: guidelines for clinical care. *Arch Surg*. 1993; 128:79-88.

Shimkue, Jamie, "Don't reinvent the wheel: Tool kit reveals true costs of surgical procedures," *OR Manager*, Jun. 2000.

Zevola, Donna R. et al., "Clinical Pathways and Coronary Artery Bypass Surgery," *Critical Care Nurse*, vol. 17, No. 6, Dec. 1997.

Fox, Irene and Brown, Todd, "Affecting Patient Care with Perioperative Clinical Pathways," *Surgical Services Management*, vol. 5, No. 10, Oct. 1999, pp. 41-47.

"JCAHO names measures for surgery," *OR Manager*, vol. 16, No. 4, Apr. 2000.

C. Farinas-Alvarez et al., "Analysis of risk factors for nosocomial sepsis in surgical patients", British Journal of Surger 2000, vol. 87, pp. 1076-1081.

R. Scott Evans, Ph.D., et al., "Prediction of Hospital Infections and Selection of Antibiotics Using an Automated Hospital Database", 14th Annual Symp. on Comp. Appl. in Medical Care, Washington DC, 1990, pp. 663-667.

Brochure entitled "Reducing the Risk of Surgical Site Infections"; 3M Health Care, (2000); No. 70-2009-3150-2 (1 pg.).

Brochure entitled "3M Sterilization Assurance Full Line Catalog—Complete sterilization assurance products"; 3M Health Care; (1998); No. 70-2009-0360-0 (782.5) DPI (39 pgs.).

Brochure entitled "Much more about sterilization process monitoring than you ever thought possible"; 3M Health Care; (1997); No. 70-2008-9626-7 (781) DPI (26 pgs.).

Brochure entitled "Prevention of Surgical Site Infections—A Consensus Document Developed by Education Design, Inc. Provided as a Service of 3M Infection Prevention"; (54 pgs.).

Mangram et al., "Guideline for the Prevention of Surgical Site Infection", *Infection Control and Hospital Epidemiology*, vol. 20, No. 4, pp. 247-278 (1999).

Arai, "Active ICN Nurses in the UK,", Igaku No Ayumi (Journal of Clinical and Experimental Medicine), Jan. 9, 1999, 9 pages, vol. 188, No. 2.

Iseki, "Present State and Future of Intraoperative Navigation by Augmented Reality," Igaku No Ayumi (Journal of Clinical and Experimental Medicine), Oct. 28, 2000, 7 pages, vol. 195, No. 4.

Oyama, "Reconsidering Perioperative Care in Measures for Handling Nosocomial Infection and Introduction of a System for Infection Prevention," (date unknown but believed to be prior to the date of the filing of the present application), 1 page.

* cited by examiner

METHODS FOR MANAGING INFECTION RISK INCIDENT TO SURGICAL PROCEDURES IN HEALTH CARE PROVIDER ENVIRONMENTS

FIELD OF THE INVENTION

The present invention relates to methods of managing the risk, occurrence, or both the risk and occurrence of surgical site infection incident to various surgical procedures. The invention also relates to devices for managing such risks, including software-encoded and network delivered devices.

BACKGROUND OF THE INVENTION

Over the past number of decades, health care environments have witnessed a nearly forty percent rise in nosocomial infections arising from the delivery of surgical procedures. This increase persists despite advances in medicine and a reduction in the number and size of hospitals. Many factors are believed to contribute to the infection rise, including the prevalence of larger intensive care units ("ICUs"), fewer nurses, the increased severity of patient illness, the increased numbers of immunocompromised patients, and the scarcity of infection control practitioners.

Surgical site infections ("SSIs") represent the third most frequently reported nosocomial infection, accounting for between 14 and 16 percent of all nosocomial infections among hospitalized patients. Among surgical patients, SSIs are the most common nosocomial infections accounting for 38 percent of such infections in this population.

The cost of a SSI to a surgical patient can be significant. The incidence of such an infection can result in extended lengths of stay, increased use of antibiotics, added pain, and longer recovery periods. Nosocomial infections also lead directly to 19,000 deaths each year and are a contributing factor to more than 80,000 additional deaths annually.

SSIs also represent additional costs to the health care system; under the majority of managed care contracts, healthcare systems are not reimbursed for the additional costs of nosocomial infections. Nosocomial infections cost health care systems $4.5 billion per year. On average, a single SSI outbreak costs $3152 and causes an additional 7.3 days of hospital stay.

Most importantly, nosocomial infections are usually preventable. With over 27 million surgical procedures performed in the U.S. each year, reducing the risk of SSIs becomes a matter of saving lives. There exists, therefore, a need for an effective and easily administerable method of managing the risk of nosocomial infections in a health care delivery facility.

SUMMARY OF THE INVENTION

Briefly, in one aspect, the present invention provides a method for managing the occurrence or risk of surgical site infection incident to a surgical procedure, the method comprising:
(a) identifying a plurality of stages of operative care, including at least a preoperative stage, an intraoperative stage, and a postoperative stage;
(b) identifying one or more points-of-care within each identified stage of operative care;
(c) for each point-of-care, identifying one or a plurality of sources of measurable risk of surgical site infection;
(d) for identified surgical site infection risks, identifying at least one practice for either or both managing or reducing the risks, either individually for each risk or collectively for more than one risk; and
(e) aligning the identified practice or practices within each point-of-care to provide a set of sequential practices throughout each of the stages of operative care in a manner that provides a desired management of the overall occurrence or risk of surgical site infection.

In another aspect, the present invention provides a method for managing the risk or occurrence of surgical site infection incident to a surgical procedure, the method comprising: (a) identifying a plurality of health care delivery practices appurtenant to a surgical procedure that contribute to or pose a risk of surgical site infection; (b) grouping one or more of the identified practices into a plurality of points-of-care; (c) aligning, monitoring and managing the operation of the points-of-care to provide a desired management of the overall occurrence or risk of surgical site infection.

In another aspect, the invention provides a system for managing the risk or occurrence of surgical site infection incident to a surgical procedure, the method comprising:
(a) identifying a plurality of stages of operative care, including at least a preoperative stage, an intraoperative stage and a postoperative stage;
(b) identifying one or more points-of-care within each identified stage of operative care;
(c) for each point-of-care, identifying one or a plurality of health care delivery practices that pose a source of measurable risk of surgical site infection;
(d) identifying one or more compliance indicators for one or a plurality of health care practices within each point-of-care whereby there is provided the ability to monitor the compliance indicators;
(e) aligning the health care delivery practices with the compliance indicators to provide a perioperative process map of delivery practices spanning the plurality of stages of operative care.

In still another aspect, the invention provides a system for managing the risk or occurrence of surgical site infection incident to a surgical procedure, the system comprising: (a) a perioperative process map of practices for the delivery of the surgical procedure, the map comprising a plurality of health care delivery practices and one or more indicators of compliance with the one or more health care practices; and (b) means for monitoring the compliance indicators to achieve a desired level of management of the risk of surgical site infection for the surgical procedure.

In still other aspects, the present invention provides devices, including software-encoded and computer network delivered devices, useful in carrying out the methods and systems of the invention.

The methods and systems of the invention can be utilized to manage or control the risk of surgical site infection and as such, they can be used to follow the course of a surgical patient from preoperative assessment when the surgical decision is made through postoperative recovery to a point when the patient is no longer at risk of infection. Moreover, the invention provides a description of actions performed by the patient and health care team involved in the patient's operation and can apply to any perioperative practice setting. Thus used, the methods and systems of the invention provide streamline approaches to a cost effective standard of care.

DETAILED DESCRIPTION OF A PREFERRED EMBODIMENT

Figure 1:
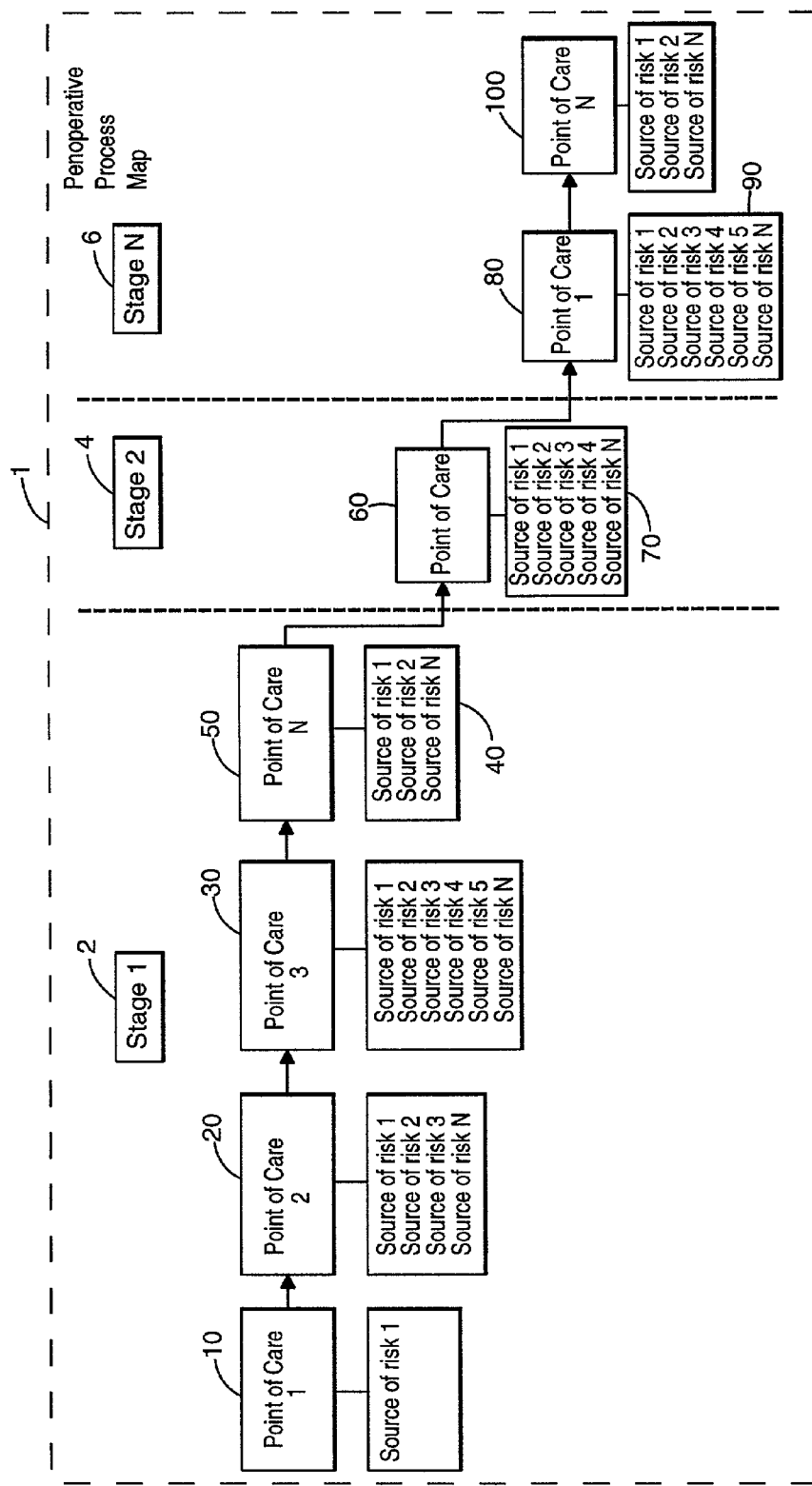
FIG. 1 illustrates a schematic perioperative process map according to the methods and systems of the invention.

The present invention provides methods and systems for managing the risk and/or occurrence of surgical site infection. In their most essential respect, the methods and systems comprise utilization of a map of health care delivery practices appurtenant to a surgical procedure, or a so-called perioperative process map. These maps can span practices delivered preoperatively, intraoperatively and post-operatively, or can be concentrated on only one or several of the stages of delivery of a surgical procedure. The perioperative maps, once envisioned, can be used in a healthcare environment to effectively manage, and in some embodiments control, the delivery of practices to reduce the risk and occurrence of surgical site infection. In so doing, the methods of the invention also impact the ability of a healthcare provider to manage other desired outcomes, including cost reduction, cost control, patient satisfaction, employee health, and employee welfare.

According to the invention, a perioperative process map is constructed for a surgical procedure of interest by identifying a plurality of stages for that surgical procedure. Depending on the scope of the desired process map, the stages may include one or more of a preoperative stage, an intraoperative stage, and a postoperative stage. Each stage of the procedure includes one or more points-of-care. These points-of-care typically comprise one or a plurality of health care practices that are delivered in relatively close proximity to one another either in time or in location. For example, a pre-operative point-of-care may include multiple preoperative activities, including administration of antibiotics, hair removal, etc., while a postoperative point-of-care may include instrument reprocessings and mechanics of environmental cleaning. While sound health care management requires that some delivery activities customarily take place in a given general order, it will be understood that each health care provider may incorporate different activities into its delivery practices, may bundle them differently into different points-of-care, and may place different activities in different sequential relation. For purposes of the present invention, however, a point-of-care for a given health care provider (and for a given surgical procedure) will include one or more closely related activities drawn together either because of their close relationship to one another in time or in place, or by their common purpose (e.g., pre-surgical patient preparation).

A point-of-care itself, combined with the activities within it, will present one or more measurable sources of infection risk. These sources may be attributable to a fixed environment. For example, the layout and ventilation of a particular surgical suite may present unique (and somewhat unalterable) sources of infection risk, while the relative proximity of the location of the administration of preoperative care to the location of a surgical suite may pose other unique risks. Other sources of risk may be more variable (and more controllable). For example, the time allowed to elapse between the administration of pre-operative regimes and the administration of the surgical procedure may be a parameter subject to control.

The methods and systems of the invention provide a mechanism to align the otherwise disconnected collection of activities necessary for the performance of a surgical procedure, categorize them according to their shared infection risk, and manage them pursuant to a common protocol for infection risk management.

FIG. 1 illustrates a generic perioperative process map according to the invention. The delivery of a surgical procedure (e.g., a coronary artery bypass graft) is segregated into N number of stages. Stage 1 comprises N points-of-care 10, 20, 30 and 50. Within each Point-of-Care N, there is identified N sources of risk 40. Stage 2 comprises a single point-of-care 60 within which there are N sources of risk 70. Similarly, Stage N comprises N points-of-care (80 and 100) comprising various sources of risk, including N sources of risk 90.

Figure 2:
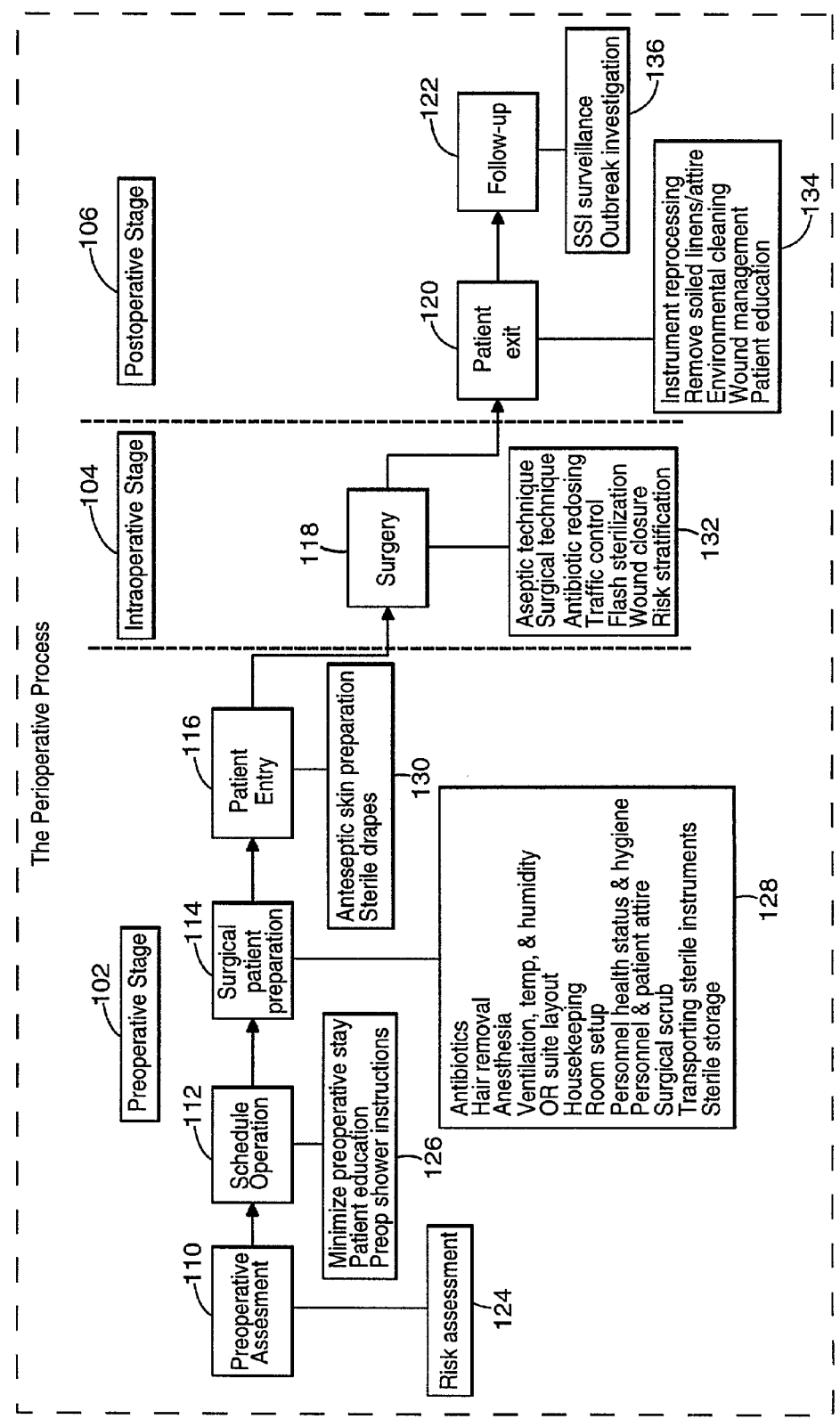
FIG. 2 illustrates one embodiment of a perioperative process map developed according to the methods and systems of the invention.

FIG. 2 illustrates another, more specific, example of a perioperative process map according to the invention. Here, the delivery of a surgical procedure is divided into three stages, a preoperative stage 102, an intraoperative stage 104 and a postoperative stage 106. The pre-operative stage comprises four points-of-care: preoperative assessment 110, operation scheduling 112, surgical patient preparation 114 and patient entry 116. Each of these points-of-care, in turn, comprise one or more activities that pose one or more measurable sources of infection risk. Point-of-care 110 comprises a single source of risk 124. Point-of-care 114 (surgical patient preparation) comprises multiple sources of risk 128. In a similar fashion, the second stage, intraoperative care 104, comprises a point-of-care 118 (surgery) within which there are seven sources of risk 132. Lastly, postoperative stage 106 comprises two points-of-care. Point-of-care 120 (patient exit) comprises five sources of risk 143 and Point-of-care 122 (patient follow-up) comprises two such measurable risk sources 136. It will be understood that the map of FIG. 1 represents and exemplifies the general structure of the perioperative process maps of the invention as applied to one possible scenario in a health care provider's facility. The map provides a tool for: (1) identifying measurable sources of infection risk (that is, those that are generally statistically significant and about which data can be gathered); and (2) aligning those sources along a continuum to set forth, for an individual provider, a generally sequential series of practices that when taken and managed together can be used to manage and/or control the risk of infection.

Figure 3:
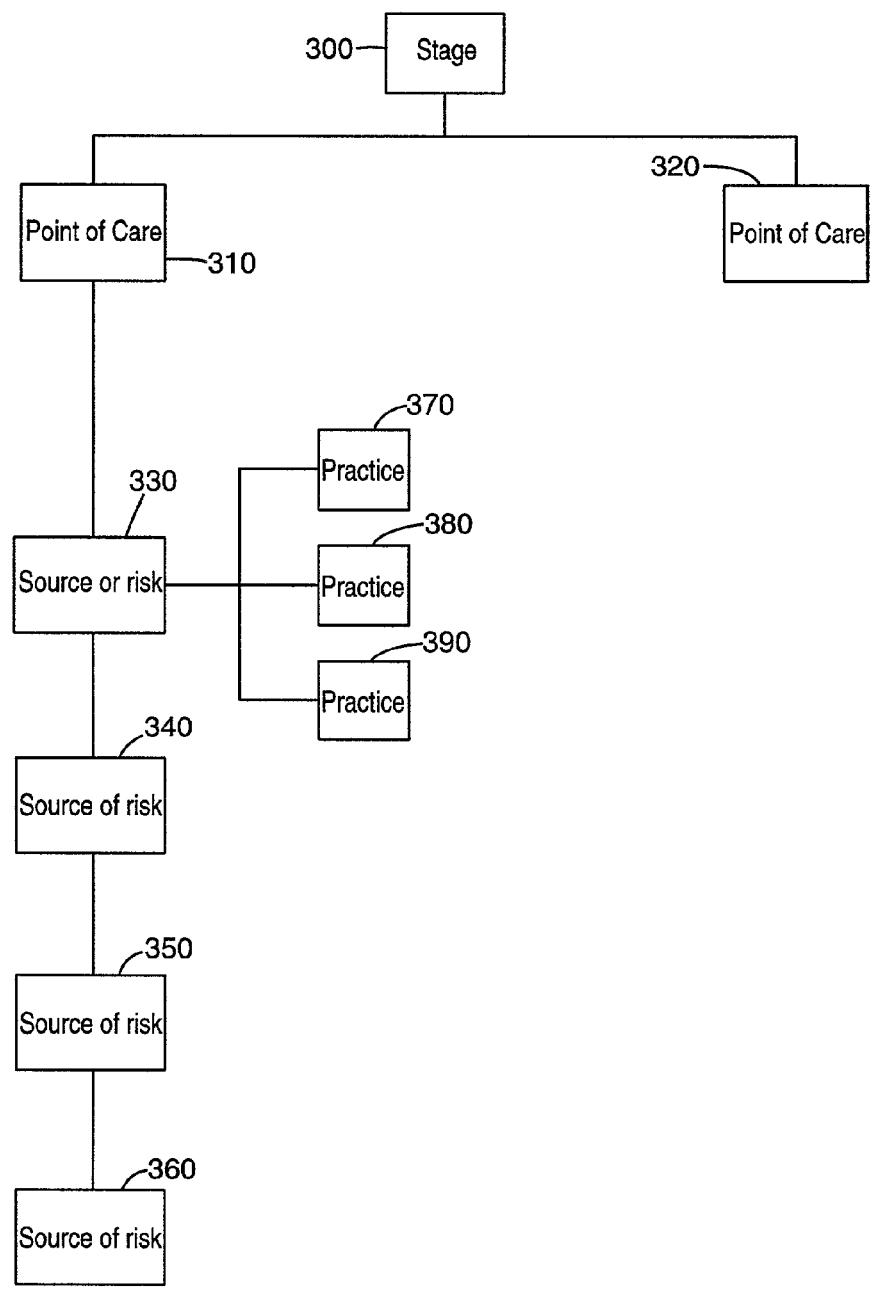
FIG. 3 provides a detailed schematic representation of one possible alignment of stages of a perioperative process map of the invention.

FIG. 3 provides a more detailed illustration of the application of a process map to one stage of a surgical procedure. Stage 300 comprises points-of-care 310 and 320. Point-of-care 310 comprises sources of risk 330, 340, 350 and 360, and source of risk 330, in turn, comprises practices 370, 380 and 390. FIG. 3 thus illustrates the generalized process map as applied, in particular, to one significant source of infection risk. Here, prudent health care judgment is applied to identify three practices delivered in one of the points-of-care that contribute to the subject source of risk. These practices are ones about which data can be generated (e.g., to identify whether or not the practice or standard was complied with or to identify the relative quality of the delivery of that practice). A more complete perioperative process map would identify a continuum of such practices.

Figure 4:
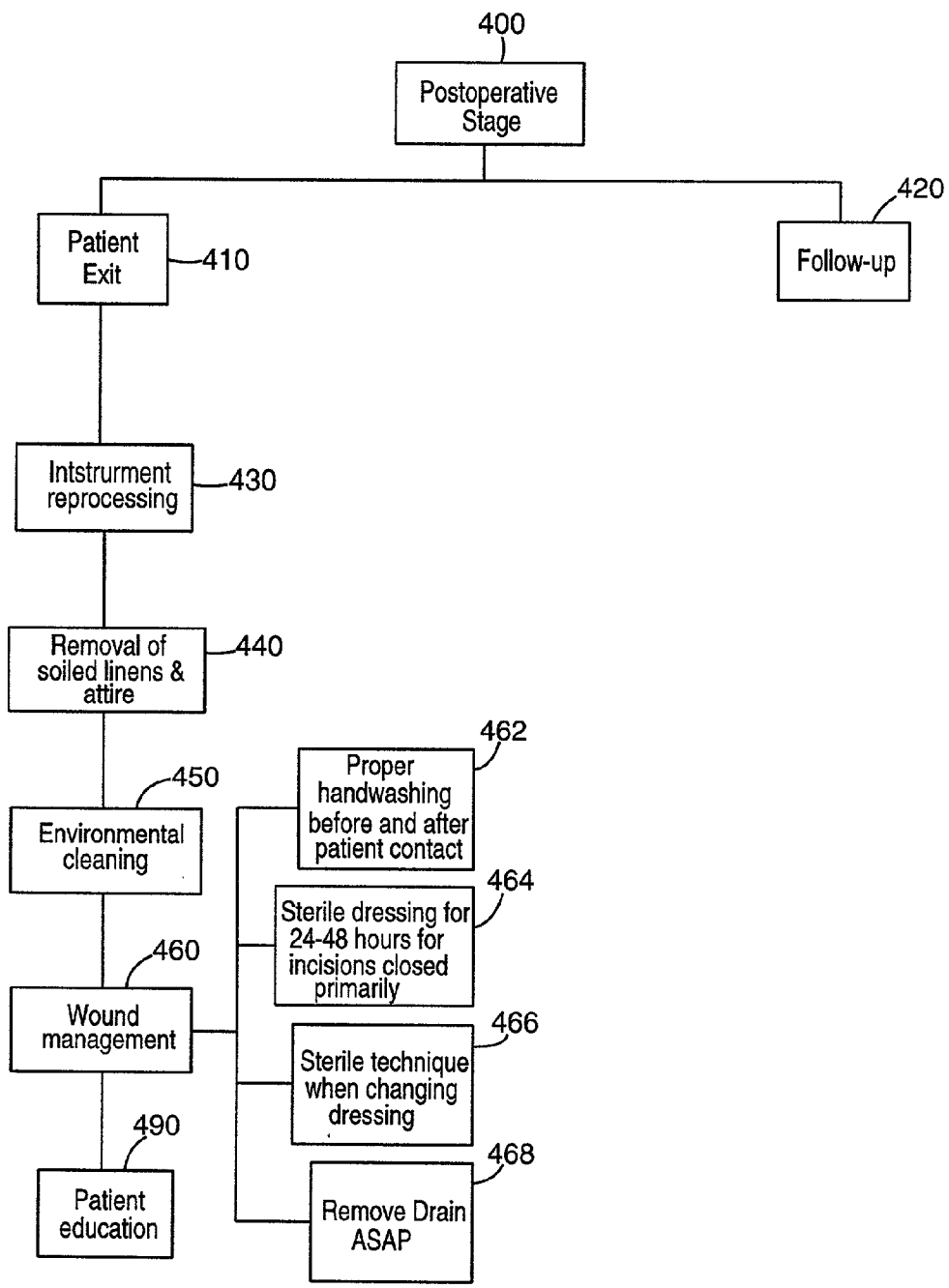
FIG. 4 illustrates one embodiment of the alignment of the stages of a perioperative process map of the invention.

FIG. 4 provides an illustration of the generalized map of FIG. 3 to one exemplary health care facility. A surgical procedure having a Postoperative stage 400 comprises two points-of-care: Patient exit from the operating room 410 and patient surgical follow-up 420. The patient exit point-of-care has five sources of measurable infection risk: risks realized from instrument reprocessing (430), soiled linen handling and removal (440), environmental cleaning (450), wound management (460) and patient education (470). In the example of FIG. 4, four practices are found to contribute to the risks attendant to wound management. These are: proper handwashing (462), administration of sterile dressings (464), dressing changing practices (466) and drain removal (468). These practices are felt to govern, in a meaningful and statistically significant way, the risks of infection for wound management in a particular hospital setting. This is not to imply that other practices (e.g., storage practices of sterile dressing) are not necessary for proper wound management, nor that such other practices may be found to be significant in another hospital setting.

The methods of the invention are generally adopted after a thorough review of a given health care facility in which the map is to be employed, most typically a traditional hospital environment. This initial review employs a prudent and knowledgeable judgment to ascertain, for a subject facility and for a given surgical procedure, what practices are to be scrutinized and categorized. Typically practices are identified according to one or several of the following characteristics: (a) practices that contribute to or pose a significant risk of infection; (b) practices that are readily measurable and controllable, (c) practices that represent or contribute a significant cost for the health care provider; and (d) practices that affect patient comfort and satisfaction. The practices that ultimately form the basis of the perioperative process map are reviewed for such characteristics and are selected according to criteria unique to the desires of the intended user. One hospital may accord different weight than another to cost control, or, within a single hospital environment, one surgical procedure may be subject to different cost considerations and constraints than another.

Once the practices are selected according to a desired set of criteria, the practices can be grouped according to their proximity with one another into points-of-care. For example, those practices that are delivered at or about the same time can be grouped together, as can those practices that are delivered in the same place or that are delivered for a common purpose or as a single regimen. Once grouped together, these practices are aligned into points-of-care and stages of care into a perioperative process map in a manner that affords a continuum of practices across one or multiple stages of care. In this way a perioperative process map can be constructed that includes all stages of surgical care, spanning from the time a surgical patient is identified as a candidate for surgery until that patient has fully recovered from the delivery of the surgical procedure and is no longer at risk for surgical site infection. This map may be referred to as a home-to-home map.

The range of possible sources of risk and health care delivery practices subject to the construction of a perioperative process map is large and, as noted above, varies from one health care facility to another and from one surgical procedure to another. It is also important to note that the delivery of a given practice may alone pose a measurable source of infection risk. In such a case, a single practice may be both a source of infection risk and a practice for managing the risk (i.e., the practice must be done in a manner that minimizes the risk it poses). Alternatively, there may be a single source of risk (e.g., risk associated with linen handling) that is appropriately managed by multiple practices (e.g., laundering, use of disposable linens, handling of soiled linens, etc.).

Table 1 below, shows some of the practices and sources of risk associated with a patient undergoing a surgical procedure.

TABLE 1

| Points-of-Care | Risk Sources/Practices |
| --- | --- |
| Home | Exercise |
| | Diet |
| | Medications |
| | Habits (smoking, etc.) |
| | Family & health history |
| Healthcare Entry | Patient history and physical |
| | Scheduling |
| | Pre-existing infection treatment |
| | Health care professional briefing |
| | Patient education and instruction |
| Preoperative Assessment | Diagnostic testing |
| | Laboratory test administration |
| | Patient education and instruction |
| | Patient risk assessment and management |
| Admission | Diagnostic studies |
| | Patient education and instruction |
| Preoperative Preparation | Preoperative shower (antiseptic or other) |
| | Hair removal method |
| | Written instructions |
| | Antibiotic prophylaxis |
| | Instrument processing |
| | Line insertions |
| | Skin preparation |
| | OR layout and set-up |
| | Equipment check |
| | Physician and nurse preparation |
| | Surgical Attire |
| | Housekeeping |
| Intraoperative Procedures | Draping |
| | Anesthesia administration |
| | Sterilization |
| | Antibiotic redosing |
| | OR traffic handling |
| | Instrument and supply transport |
| | Surgical field sterility |
| | Duration of operation |
| | Room cleaning and filtering |
| | Surgical technique |
| | Aseptic technique |
| | Wound closure |
| | Risk stratification |
| Postoperative Recovery | Patient education and instruction |
| | Room cleaning and filtering |
| | Instrument reprocessing and storage |
| | Needs assessment |
| | Skin integrity |
| | Wound care |
| | Soiled attire and linen handling |
| Discharge | Patient education and instruction |
| | Patient compliance in diet |
| | Patient compliance in medication |
| | Patient compliance in wound management |
| Physician Follow-up | Health assessment |
| | SSI surveillance |
| | Scheduling of routine care |
| | Health promotion |
| | Infection outbreak management |
| Home | Healthy living |

In some embodiments, the methods and systems of the invention incorporate avenues for monitoring the level and degree of compliance with the perioperative process map in practice settings. Briefly, according to this aspect of the invention, one or more of the health care delivery practices and/or sources of risk are monitored with one or more compliance indicators. These compliance indicators typically will measure or mark the delivery of the subject practice or practices (or the management of the source or sources of risk) against an accepted standard. A compliance indicator may, for example, ask whether or not a practice has been performed, or it may seek a qualified or quantified measure of the quality of the performed practice. Standards of care against which compliance indicators may be selected are drawn from any number of accepted protocols, guidelines, standards or clinical pathways, including those identified below, which are incorporated by reference herein in their entirety.

American Association of Nurse Anesthetists (AANA), *Infection Control Guide*, Park Ridge, Ill.: AANA; revised 1997.

American College of Surgeons, Care of the Surgical Patient, Volume 2: Elective Care, New York, N.Y.: Scientific American; 1988-1993.

American Institute of Architects, Academy of Architecture for Health, with assistance from the U.S. Department of Health and Human Services, *Guidelines for Design and Construction of Hospital and Health Care Facilities*, Washington, D.C.: AIA Press; 1996.

American Society of Anesthesiologists (ASA), Committee on Occupational Health of Operating Room Personnel and Task Force on Infection Control, Recommendation for Infection Control for the Practice of Anesthesiology, $2^{nd}$ ed., Available at www.asahq.org/profinfo/infection.

Association for Professionals in Infection Control and Epidemiology (APIC), Larson E L. APIC guideline for handwasing and hand antisepsis in health are settings, *Am J Infect Control*. 1995; 23:251-269.

Larson E. Guideline for use of topical antimicrobial agents. *Am J Infect Control*. 1988; 16:253-266.

Lee T B, Baker O G, Lee J T, Scheckler W E, Steele L, Laxton C E. Recommended practices for surveillance. *Am J Infect Contol*. 1998; 26:277-288.

Martin M A, Reichelderfer M. APIC guideline for infection prevention and control in flexible endoscopy. *Am J Infect Control*. 1994; 22:19-38.

Rutala W A. APIC guideline for selection and use of disinfectants. *Am J Infect Control*. 1996; 24:313-342.

Sherertz R J, Streed S A, Gledhill K S. Surgical site infections. In APIC *Infection Control and Applied Epidemiology*. St. Louis, Mo.: Mosby; 1996:11-1 to 11-5.

Association for the Advancement of Medical Instrumentation (AAMI), *AAMI Standards and Recommended Practices, Volume* 1.1: *Sterilization*. Arlington, Va.:AAMI; 1998.

Association of periOperative Registered Nurses (AORN), *Recommended Practices & Guidelines*. Denver, Colo.: AORN; 1999.

Centers for Disease Control and Prevention, Hospital Infection Control Practices Advisory Committee (CDC), Mangram A J, Horan T C, Pearson M L, et al. Guideline for prevention of surgical site infection, 1999. *Am J Infect Control*. 1999; 27:97-134.

Society for Healthcare Epidemiology of America (SHEA), Consensus paper on the surveillance of surgical wound infections: The Society for Hospital Epidemiology of America, The Association of Practitioners in Infection Control, The Centers for Disease Control, The Surgical Infection Society. *Infect ControlHosp Epidemiol*. 1992; 13:599-605.

Surgical Infection Society (SIS), Page C P, Bohen J M, Fletcher J R, et al. Antimicrobial prophylaxis for surgical wounds: guidelines for clinical care. *Arch Surg*. 1993; 128: 79-88.

Figure 5:
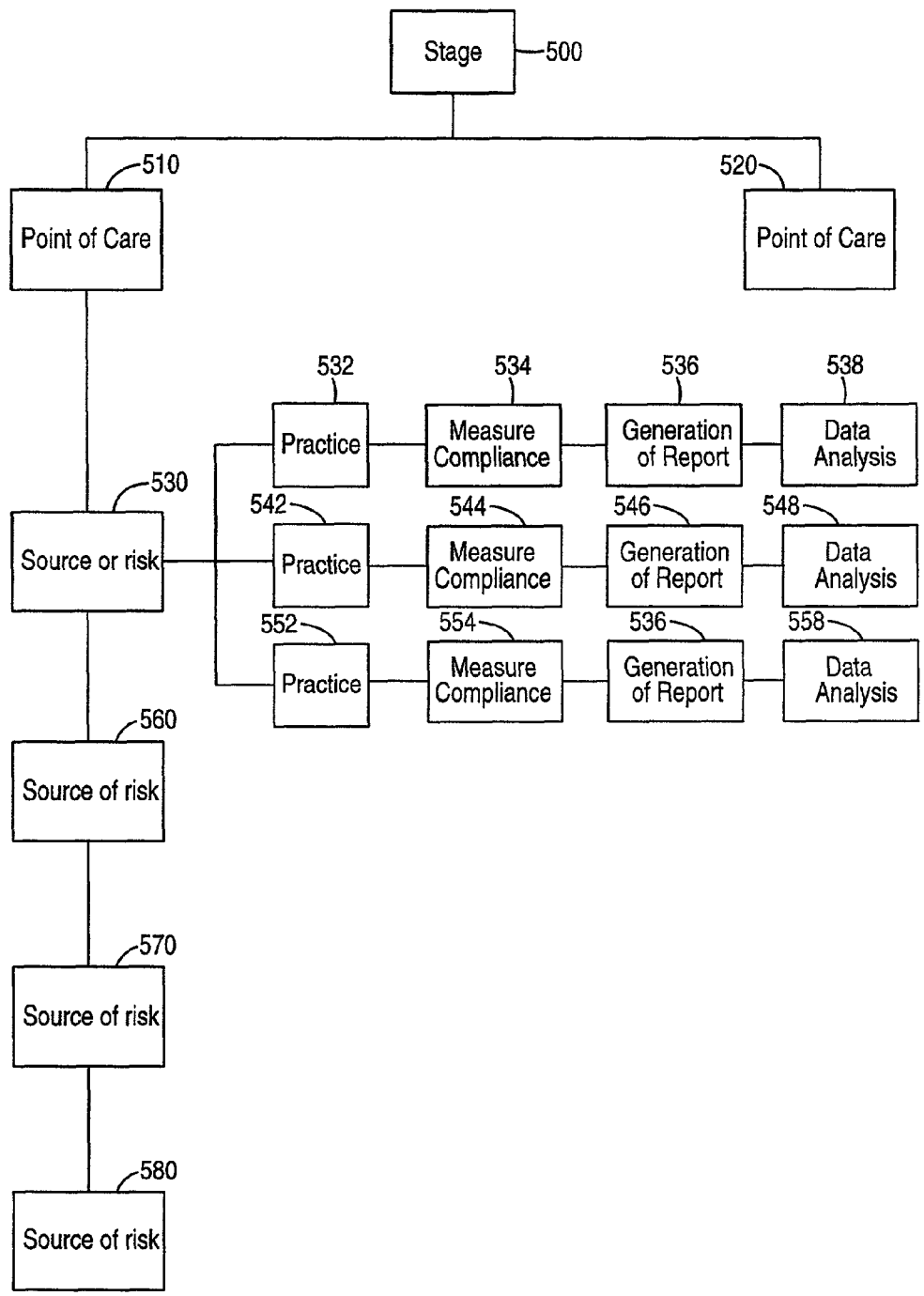
FIG. 5 illustrates an embodiment of a perioperative process map utilizing compliance indication techniques according to the invention.

FIG. 5 illustrates the operation of a perioperative process map according to the invention that incorporates the use of compliance indicators. In FIG. 5, Stage of care 500 comprises two points-of-care 510 and 520. Point-of-care 510 comprises in turn four sources of risk 530, 560, 570 and 580. Source of risk 530 is identified as having three practices 532, 542, and 552 that contribute to that risk. For each identified practice a compliance indicator is selected and measured (as indicated by steps 534, 544, and 554). As noted above, this measurement may take the form of a simple indication that a practice was performed or may represent a selection against a pre-established quality scale (e.g., a numeric scale from 1 to 10). From these measurements, reports 536, 546 and 556 may be generated. These reports may represent a simple compilation of measurement data. They may also involve or represent manipulation of the raw data, by formula or otherwise, to transform the data into a desired finished or near-finished form. These reports may then be used as inputs to data analyses 538, 548 and 558. Such data analyses can be used in any manner desired by the user. For example, the data compilations may be used simply to monitor compliance with the perioperative process map in real-time, to record historical trends in compliance, to correlate the compliance indicators with one or more indications of a desired outcome (e.g., infection rate, cost control, or patient satisfaction), or as inputs to one or more feedback process control loops. The data compilations can also be used for multiple such uses.

Figure 6:
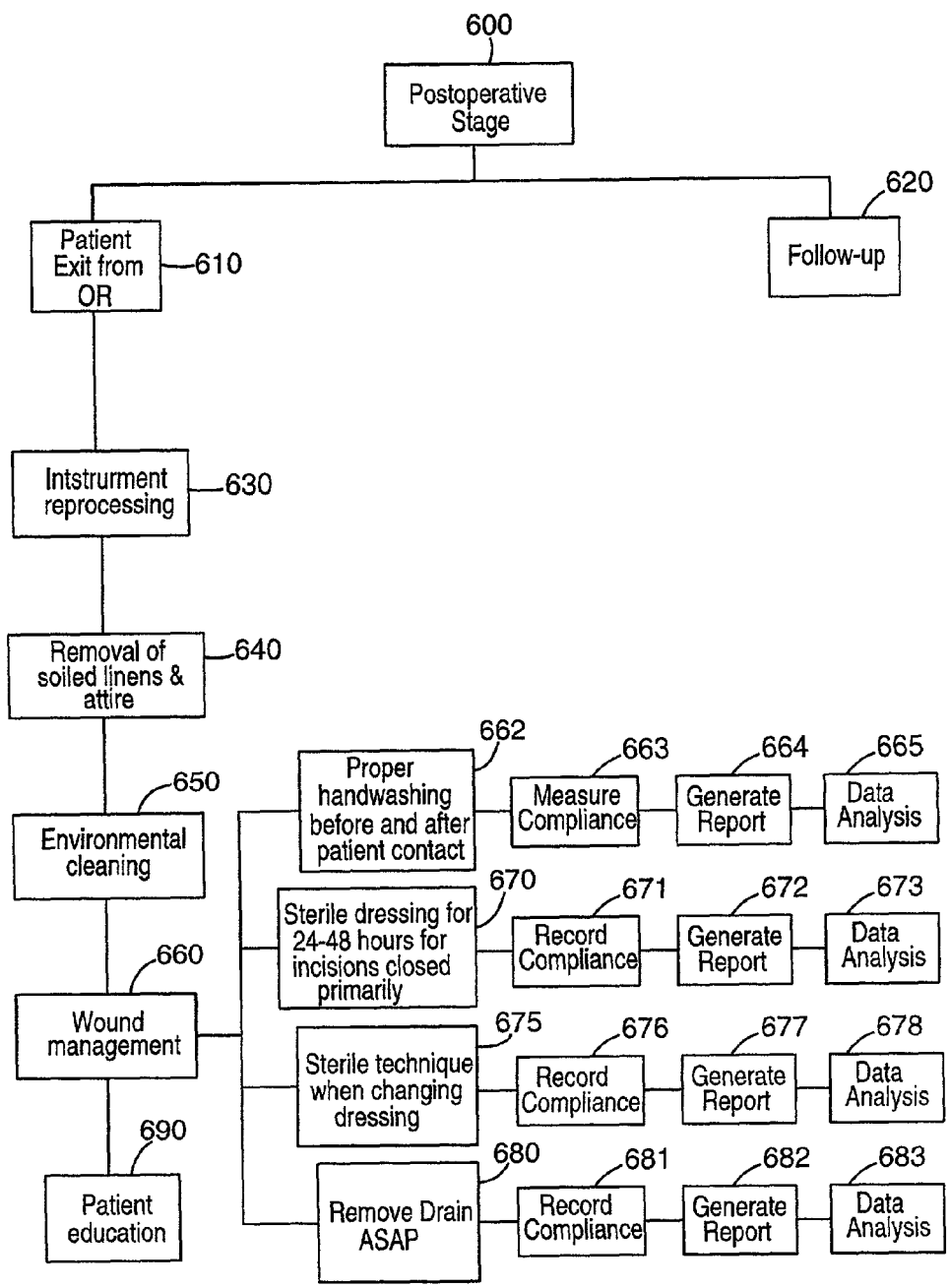
FIG. 6 illustrates one possible application of the use of compliance indication according to the invention to a post-operative stage of care.

FIG. 6 illustrates one possible application of a system employing compliance indicator measurement to a postoperative stage of care. In FIG. 6, Postoperative Stage 600 comprises two points-of-care 610 and 620, patent exit from OR and patient follow-up respectively. In turn, point-of-care 610 comprises five significant sources of risk, instrument reprocessing 630, removal of soiled linen and attire 640, environmental cleaning 650, wound management 660 and patent education 690. Source 660 (wound management) comprises four practices: handwashing 662, dressing application timing 670, dressing application technique 675 and drain removal 680. According to the illustrated embodiment, compliance of each practice is measured and recorded (as indicated by reference numerals 664, 672, 677 and 682) from which reports are generated (664, 672, 677 and 682) and the resulting data is analyzed (665, 673, 678 and 683) according to the needs and desires of the user.

Figure 7:
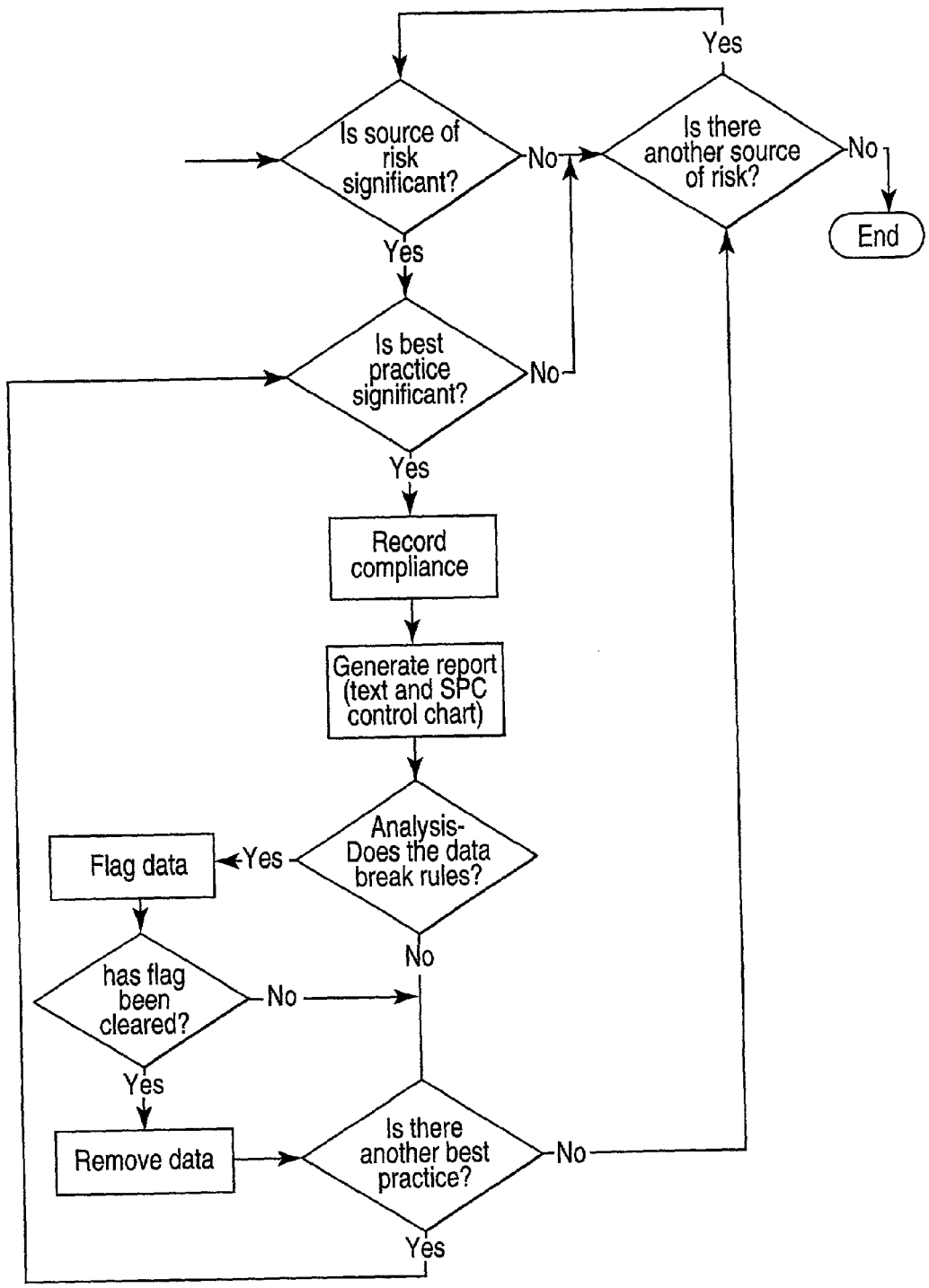
FIG. 7 illustrates one possible implementation of compliance indication to the methods and systems of the invention.
Figure 5:
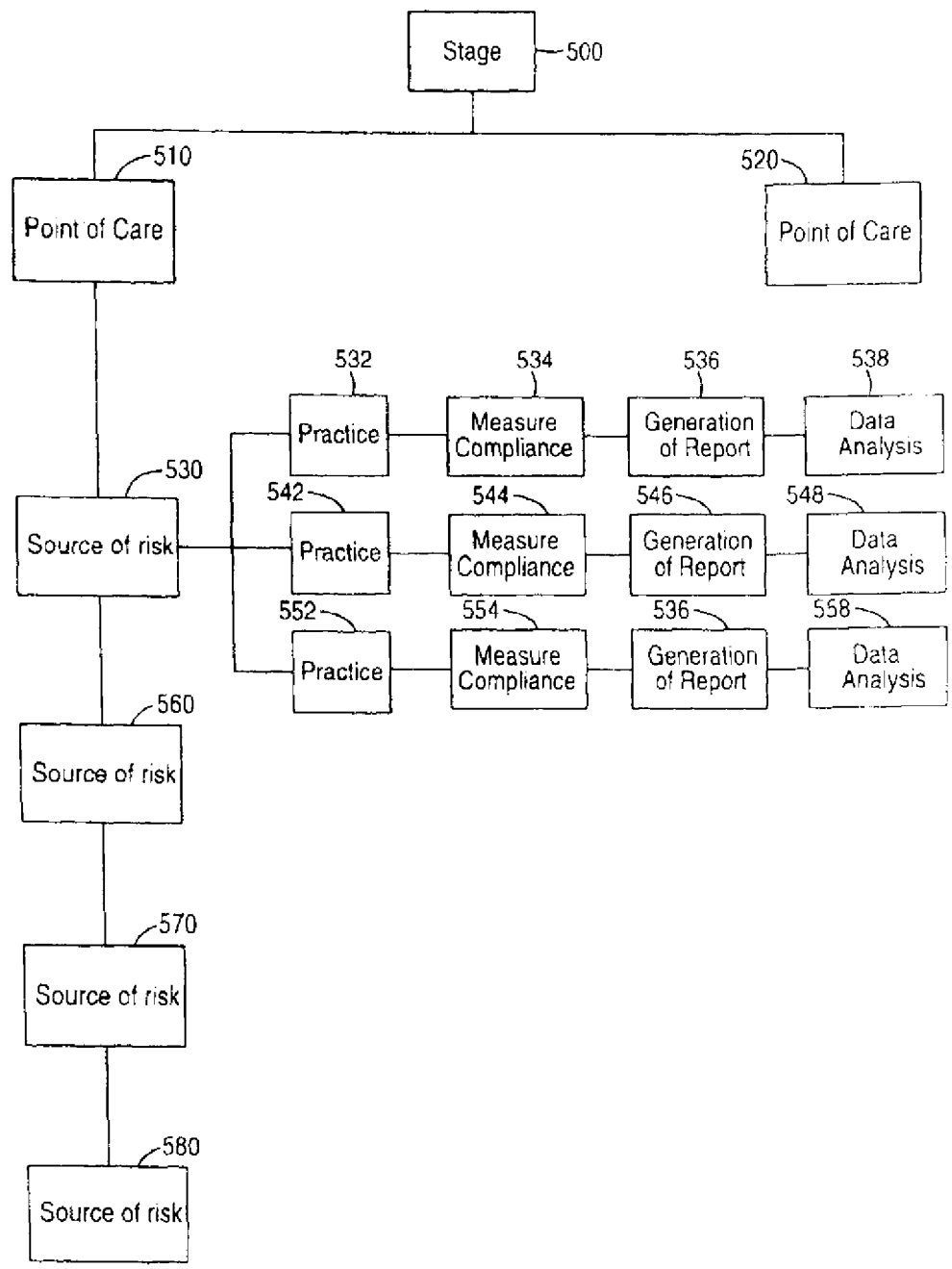

The methods and systems of the invention can be, in part or in whole, encoded into software or hardware. Thus, devices can be constructed which embody the perioperative process maps of the invention. Such devices may find particular utility in managing and monitoring systems of the invention that employ one or more compliance indicators and/or one or more outcome indicators (e.g., patient satisfaction, infection rate, etc.). Such software, when used, can be encoded by any known or useful method and can utilize any known or useful software language. FIG. 7 shows one possible embodiment of encoded logic. Briefly, in such an embodiment, a practice is evaluated for the significance of the risk it poses. For those risks that are determined to pose a significant infection risk, one or more compliance indicators are measured and recorded. The recorded compliance data is analyzed and compared against a standard (or rule). For any practice not in compliance, data is flagged and action must be taken (the nature of which may be determined by the user) to clear the flag.

Software-encoded devices may be used as part of an effective risk management program. Such devices can be incorporated into other software regimes, including software that tracks and manages the flow of patients throughout a health care facility. The software devices of the invention can also be used for remote monitoring of a health care facility, e.g., monitoring done for the health care facility by individuals located off-site from the facility. Such devices could operate across a computer network or via the internet.

Various modifications and alterations of this invention will be apparent to those skilled in the art without departing from the scope and spirit of this invention, and it should be understood that this invention is not limited to the illustrative embodiments set forth herein.

We claim:

1. A computer-implemented system for managing the risk or occurrence of surgical site infection incident to a surgical procedure, the computer-implemented system comprising: one or more computers, one or more non-transitory computer readable memories storing:

a module configured to identifying a plurality of stages of operative care associated with the surgical procedure, including at least a preoperative stage, an intraoperative stage and a postoperative stage;

a module configured to identifying one or more points-of-care within each identified stage of operative care associated with the surgical procedure;

for each point-of-care associated with the surgical procedure, a module configured to identifying one or a plurality of health care delivery practices associated with the surgical procedure that pose a source of measurable risk of surgical site infection, wherein the health care delivery practices associated with the surgical procedure that pose a source of measurable risk of surgical site infection are selectable for a given health care facility;

a module configured to identifying one or more compliance indicators associated with the surgical procedure for the one or plurality of health care delivery practices associated with the surgical procedure within each point-of-care associated with the surgical procedure whereby there is provided the ability to monitor the compliance indicators, wherein at least some of the compliance indicators quantify a measure of quality associated with delivery of corresponding health care delivery practices; and for each of the compliance indicators, a computer-implemented module configured to generating a flag when a given health care delivery practice associated with the surgical procedure is not in compliance with a rule to thereby align the health care delivery practices associated with the surgical procedure into rule compliance and to provide a perioperative process map of delivery practices spanning the plurality of stages of operative care associated with the surgical procedure to thereby manage the risk or occurrence of surgical site infection incident to the surgical procedure.

2. A system for managing the risk or occurrence of surgical site infection incident to a surgical procedure, the system comprising: one or more computers, one or more non-transitory computer readable memories storing:

a module configured to identifying one or more health care delivery practices associated with the surgical procedure that pose a source of measurable risk of surgical site infection, wherein the health care delivery practices associated with the surgical procedure that pose a source of measurable risk of surgical site infection are selectable for a given health care facility;

a module configured to identifying one or more compliance indicators associated with the surgical procedure for the one or plurality of health care delivery practices associated with the surgical procedure within each point-of-care associated with the surgical procedure, wherein at least some of the compliance indicators quantify a measure of quality associated with delivery of corresponding health care delivery practices;

a module configured to constructing a perioperative process map of practices for the delivery of the surgical procedure, the map comprising the one or more health care delivery practices associated with the surgical procedure and the one or more indicators of compliance with the one or more health care practices; and a computer-implemented module configured to monitoring the compliance indicators to achieve a desired level of management of the risk of surgical site infection for the surgical procedure, wherein the computer-implemented module configured to monitoring the compliance indicators generates a flag when a given health care practice associated with the surgical procedure is not in compliance with a rule to thereby manage the risk of surgical site infection incident to the surgical procedure.

3. The system of claim 2 further comprising a module configured to recording the compliance indicators.

4. The system of claim 2 wherein the computer-implemented module configured to monitoring comprises a software-encoded information management device.

5. The system of claim 4 wherein the information management device is delivered to one or more users via the internet.

6. The system of claim 2 wherein the computer-implemented module configured to monitoring comprises a software-encoded information management device that is capable of operating across a network of computers.

7. The system of claim 2 further comprising a module configured to monitoring one or more indicators of outcome.

8. The system of claim 7 wherein the outcome is the rate of the incidence of surgical site infection.

9. The system of claim 7 wherein the outcome is the patient satisfaction.

10. The system of claim 7 wherein the outcome is cost.

11. A computer-implemented method for managing risks of surgical site infection incident to a surgical procedure, the method comprising:

selecting, via a computer, for a given health care facility a plurality of health care delivery practices associated with the surgical procedure that pose a source of measurable risk of surgical site infection;

evaluating, via the computer, a given one of the practices associated with the surgical procedure that poses an infection risk during a stage of the surgical procedure;

storing, via the computer, data indicative of the given practice associated with the surgical procedure as executed by one or more persons involved with the surgical procedure;

identifying via a compliance indicator when the data indicative of the given practice associated with the surgical procedure is not in compliance with a rule established for the given practice to thereby manage risks of surgical site infection incident to the surgical procedure, wherein the compliance indicator quantifies a measure of quality associated with delivery of the given practice; and generating, via the computer, a flag associated with the compliance indicator when the given practice associated with the surgical procedure is not in compliance with a rule established for the given practice to thereby align the given practice into rule compliance.

12. The method of claim 11, further comprising prompting medical personnel to take further action when the flag is generated.

13. The method of claim 12, further comprising clearing the flag when the further action is taken.

14. The method of claim 11, further comprising generating a perioperative process map of a plurality of practices in a plurality of stages, the plurality of stages including at least a prepoperative stage, an intraoperative stage, and a postoperative stage.

15. The method of claim 14, further comprising for each stage of the perioperative process map:
evaluating practices that pose infection risks during the given stage of the surgical procedure;
storing data indicative of each of the practices as executed by one or more persons involved with the surgical procedure; and
identifying when the data indicative of any of the practices is not in compliance with a rule established for the given practice.

16. The method of claim 15, wherein identifying when the data indicative of any of the practices is not in compliance with the rule established for the given practice comprises generating a flag for the data indicative of one of the practices not in compliance with the rule established for that practice.

17. The method of claim 16, further comprising prompting medical personnel to take further action when the flag is generated.

18. The method of claim 17, further comprising clearing the flag when the further action is taken.

19. The method of claim 11, wherein the computer-implemented method is implemented by the computer in hardware.

20. The method of claim 11, further comprising:
evaluating each of a plurality of practices associated with the surgical procedure that pose infection risks during the surgical procedure;
storing data indicative of each of the practices as executed by one or more persons involved with the surgical procedure; and
identifying when the data indicative of one or more of the practices associated with the surgical procedure is not in compliance with a respective rule established for a respective practice.

21. The method of claim 11, further wherein the compliance indicator defines a value within a pre-established quality scale.

22. The method of claim 21, wherein the quality scale ranges from 1 to 10.

23. The method of claim 11, further comprising generating a report that represents a compilation of measurement data associated with the surgical procedure.

24. A computer-implemented system for managing risks of surgical site infection incident to a surgical procedure, the system comprising: one or more computers, one or more non-transitory computer readable memories storing:
a module configured to selecting for a given health care facility a plurality of health care delivery practices associated with the surgical procedure that pose a source of measurable risk of surgical site infection;
a module configured to evaluating a given one of the practices associated with the surgical procedure that poses an infection risk during a stage of the surgical procedure;
a computer-implemented module configured to storing data indicative of the given practice associated with the surgical procedure as executed by one or more persons involved with the surgical procedure;
a computer-implemented module configured to identifying via a compliance indicator when the data indicative of the given practice associated with the surgical procedure is not in compliance with a rule established for the given practice to thereby manage risks of surgical site infection incident to the surgical procedure, wherein the compliance indicator quantifies a measure of quality associated with delivery of the given practice; and
a computer-implemented module configured to generating a flag associated with the compliance indicator when the given practice associated with the surgical procedure is not in compliance with a rule established for the given practice to thereby align the given practice associated with the surgical procedure into rule compliance.

25. The system of claim 24, further comprising a module configured to prompting medical personnel to take further action when the flag is generated.

26. The system of claim 25, further comprising a module configured to clearing the flag when the further action is taken.

27. The system of claim 24, further comprising a module configured to generating a perioperative process map of a plurality of practices in a plurality of stages, the plurality of stages including at least a prepoperative stage, an intraoperative stage, and a postoperative stage.

28. The system of claim 27, further comprising for each stage of the perioperative process map:
a module configured to evaluating practices that pose infection risks during the given stage of the surgical procedure;
a module configured to storing data indicative of each of the practices as executed by one or more persons involved with the surgical procedure; and
a module configured to identifying when the data indicative of any of the practices is not in compliance with a rule established for the given practice.

29. The system of claim 24, further comprising a module configured to prompting medical personnel to take further action when the flag is generated.

30. The system of claim 29, further comprising a module configured to clearing the flag when the further action is taken.

31. The system of claim 24, further comprising:
a module configured to evaluating each of a plurality of practices associated with the surgical procedure that pose infection risks during the surgical procedure;
a module configured to storing data indicative of each of the practices as executed by one or more persons involved with the surgical procedure; and
a module configured to identifying when the data indicative of one or more of the practices associated with the surgical procedure is not in compliance with a respective rule established for a respective practice.

32. The system of claim 24, further wherein the compliance indicator defines a value within a pre-established quality scale.

33. The system of claim 32, wherein the quality scale ranges from 1 to 10.

34. The system of claim 24, further comprising a computer-implemented module configured to generating a report that represents a compilation of measurement data associated with the surgical procedure.

* * * * *

UNITED STATES PATENT AND TRADEMARK OFFICE
CERTIFICATE OF CORRECTION

PATENT NO. : 8,447,624 B2
APPLICATION NO. : 09/729034
DATED : May 21, 2013
INVENTOR(S) : Pederson et al.

It is certified that error appears in the above-identified patent and that said Letters Patent is hereby corrected as shown below:

The title page showing the illustrative figure should be deleted to be replaced with the attached title page.

Title Page 2
Column 1 (Other Publications); Line 8, Delete "health are" and insert -- health care --, therefor.

In the Drawings:
In the drawing sheets, consisting of Fig. 5, should be deleted to be replaced with the drawing sheet, consisting of Fig. 5, as shown on the attached pages.

Sheet 1 of 7 (Fig. 1)
Line 1; Delete "penoperative" and insert -- perioperative --, therefor.

Sheet 3 of 7 (Reference Numeral 330) (Fig. 3)
Line 1; Delete "Source or risk" and insert -- Source of risk --, therefor.

Sheet 4 of 7 (Reference Numeral 430) (Fig. 4)
Line 1; Delete "Intstrument" and insert -- Instrument --, therefor.

Sheet 5 of 7 (Reference Numeral 530) (Fig. 5)
Line 1; Delete "Source or risk" and insert -- Source of risk --, therefor. (see attached)

Sheet 6 of 7 (Reference Numeral 630) (Fig. 6)
Line 1; Delete "Intstrument" and insert -- Instrument --, therefor.

In the Specification:
Column 7
Line 24-25; Delete "handwasing" and insert -- handwashing --, therefor.
Line 25; Delete "health are" and insert -- health care --, therefor.
Line 31; Delete "Contol." and insert -- Control. --, therefor.

Signed and Sealed this
Fifth Day of November, 2013

Teresa Stanek Rea
*Deputy Director of the United States Patent and Trademark Office*

(12) United States Patent
Pederson et al.

(10) Patent No.: US 8,447,624 B2
(45) Date of Patent: May 21, 2013

(54) METHODS FOR MANAGING INFECTION RISK INCIDENT TO SURGICAL PROCEDURES IN HEALTH CARE PROVIDER ENVIRONMENTS

(75) Inventors: Cheryl A. Pederson, Eden Prairie, MN (US); Jennifer S. Ma, St. Paul, MN (US); Nancy J. Dyslin, Stillwater, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 1873 days.

(21) Appl. No.: 09/729,034

(22) Filed: Dec. 4, 2000

(65) Prior Publication Data
US 2002/0103671 A1 Aug. 1, 2002

(51) Int. Cl.
G06Q 50/00 (2012.01)

(52) U.S. Cl.
USPC ............................................................ 705/2

(58) Field of Classification Search .... 705/2–4; 600/300
See application file for complete search history.

(56) References Cited

U.S. PATENT DOCUMENTS

| | | | | |
|---|---|---|---|---|
| 5,562,448 | A * | 10/1996 | Mushabac | 433/215 |
| 5,937,364 | A * | 8/1999 | Westgard et al. | 702/83 |
| 6,157,853 | A * | 12/2000 | Blume et al. | 600/426 |
| 6,509,730 | B1 * | 1/2003 | Afsah | 324/158.1 |
| 6,662,081 | B1 * | 12/2003 | Jacober et al. | 700/242 |
| 6,827,670 | B1 * | 12/2004 | Stark et al. | 482/9 |
| 2002/0077865 | A1 * | 6/2002 | Sullivan | 705/3 |

FOREIGN PATENT DOCUMENTS

| | | |
|---|---|---|
| JP | 11-85876 A | 3/1999 |
| WO | 00/67189 | 11/2000 |

OTHER PUBLICATIONS

Mangram et al., "Guideline for the Prevention of Surgical Site Infection", American Journal of Infection Control, 1999, vol. 27, pp. 97-134.*
Ormond-Walshe, Sarah, "Computerised databases in infection control", Nursing Standard, Jan. 2000, vol. 14, No. 18, pp 43.*
Skledar et al., "Using a CQI process to change surgical antimicrobial prophylaxis practices", Formulary, Jan. 2000, vol 35, No. 1, pp 53.*
Guebbels et al., "An operating surveillance system of surgical site infections in the Netherlands: Results of the PREZIS National Surveillance Network", Infection Control & Hospital Epidemiology, May 2000, vol. 21, No. 5, pp 311.*
American Association of Nurse Anesthetists (AANA), *Infection Control Guide*, Park Ridge, IL: AANA; revised 1997.
American College of Surgeons, Care of the Surgical Patient, vol. 2. Elective Care. New York, NY: Scientific American; 1988-1993.
American Institute of Architects, Academy of Architecture for health, with assistance from the U.S. Department of Health and Human Services, *Guidelines for Design and Construction of Hospital and Health Care Facilities*, Washington, D.C. AIA Press; 1996.

(Continued)

*Primary Examiner* — Gerald J. O'Connor
*Assistant Examiner* — John Pauls
(74) *Attorney, Agent, or Firm* — X. Christina Huang

(57) ABSTRACT

The invention provides methods and systems designed generally to managing the risk or occurrence of surgical site infection incident to a surgical procedure. The methods and systems employ perioperative process mapping tools that align, monitor and/or manage the operation of a plurality of health care delivery practices and thereby provide a desired level of infection risk management.

34 Claims, 7 Drawing Sheets